United States Patent
Edamura et al.

(10) Patent No.: US 10,574,030 B2
(45) Date of Patent: Feb. 25, 2020

(54) EXTERNAL RESONANCE TYPE LASER MODULE, ANALYSIS APPARATUS, METHOD OF DRIVING EXTERNAL RESONANCE TYPE LASER MODULE, AND NON-TRANSITORY COMPUTER READABLE MEDIUM

(71) Applicant: HAMAMATSU PHOTONICS K.K., Hamamatsu-shi, Shizuoka (JP)

(72) Inventors: Tadataka Edamura, Hamamatsu (JP); Atsushi Sugiyama, Hamamatsu (JP); Tatsuo Dougakiuchi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 16/051,547

(22) Filed: Aug. 1, 2018

(65) Prior Publication Data

US 2019/0052058 A1 Feb. 14, 2019

(30) Foreign Application Priority Data

Aug. 10, 2017 (JP) ................. 2017-155329

(51) Int. Cl.
*H01S 5/14* (2006.01)
*H01S 5/026* (2006.01)
*G01J 3/10* (2006.01)
*G01J 3/42* (2006.01)
*H01S 5/062* (2006.01)
(Continued)

(52) U.S. Cl.
CPC ............... *H01S 5/141* (2013.01); *G01J 3/10* (2013.01); *G01J 3/42* (2013.01); *H01S 5/0264* (2013.01); *H01S 5/0622* (2013.01); *H01S 5/06216* (2013.01); *H01S 5/06255* (2013.01); *H01S 5/3401* (2013.01); *B81B 2201/047* (2013.01); *G01J 2003/423* (2013.01); *G01N 21/39* (2013.01)

(58) Field of Classification Search
CPC ...... H01S 5/141; H01S 5/0264; H01S 5/3401; H01S 5/06255; B81B 2201/047
See application file for complete search history.

(56) References Cited

U.S. PATENT DOCUMENTS

| | | | |
|---|---|---|---|
| 6,690,690 B2 * | 2/2004 | Marron | H01S 5/141 372/107 |
| 6,856,632 B1 * | 2/2005 | Heanue | H01S 5/141 372/101 |

(Continued)

*Primary Examiner* — Yuanda Zhang
(74) *Attorney, Agent, or Firm* — Drinker Biddle & Reath LLP (57) ABSTRACT

An external resonance type laser module includes a quantum cascade laser, a MEMS diffraction grating configured to include a diffraction/reflection portion configured to diffract and reflect light emitted from the quantum cascade laser and return a part of the light to the quantum cascade laser by swinging the diffraction/reflection portion, and a controller configured to control driving of the quantum cascade laser. The controller is configured to pulse-drive the quantum cascade laser such that pulsed light of a second frequency higher than a first frequency at which the diffraction/reflection portion swings is emitted from the quantum cascade laser and a phase of the pulsed light changes each time the diffraction/reflection portion reciprocates m times (m: an integer of 1 or more).

8 Claims, 8 Drawing Sheets

(51) Int. Cl.
*H01S 5/0625* (2006.01)
*H01S 5/34* (2006.01)
*G01N 21/39* (2006.01)

(56) References Cited

U.S. PATENT DOCUMENTS

| | | | |
|---|---|---|---|
| 6,912,235 B2 * | 6/2005 | Anthon | H01S 5/141 |
| | | | 372/18 |
| 7,012,696 B2 * | 3/2006 | Orr | G01J 3/42 |
| | | | 356/437 |
| 7,903,704 B2 | 3/2011 | Patel et al. | |
| 2003/0007523 A1 * | 1/2003 | Chapman | H01S 5/141 |
| | | | 372/20 |
| 2008/0159341 A1 * | 7/2008 | Patel | B82Y 20/00 |
| | | | 372/20 |
| 2009/0213882 A1 * | 8/2009 | Weida | G01N 21/3504 |
| | | | 372/23 |
| 2012/0033220 A1 * | 2/2012 | Kotidis | B82Y 20/00 |
| | | | 356/445 |
| 2016/0336720 A1 * | 11/2016 | Schenk | G01J 3/108 |

* cited by examiner

EXTERNAL RESONANCE TYPE LASER MODULE, ANALYSIS APPARATUS, METHOD OF DRIVING EXTERNAL RESONANCE TYPE LASER MODULE, AND NON-TRANSITORY COMPUTER READABLE MEDIUM

TECHNICAL FIELD

An aspect of the present disclosure relates to an external resonance type laser module, an analysis apparatus, a method of driving the external resonance type laser module, and a program.

BACKGROUND

An external resonance type laser module including a quantum cascade laser and a diffraction grating for diffracting and reflecting light emitted from the quantum cascade laser has been known as a light source used for spectroscopic analysis and used to perform wavelength sweeping (scanning). In such an external resonance type laser module, for example, the diffraction grating is fixed on a rotation stage, and the rotation stage is rotated by an actuator to change a direction of the diffraction grating, whereby a wavelength of output light is variable (for example, see U.S. Pat. No. 7,903,704).

The external resonance type laser module described above is required to be able to realize highly accurate measurement when used for spectroscopic analysis while attempting miniaturization and improvement in reliability.

SUMMARY

An object of an aspect of the disclosure is to provide an external resonance type laser module capable of realizing highly accurate measurement when used for spectroscopic analysis while attempting miniaturization and improvement in reliability.

An external resonance type laser module according to an aspect of the disclosure includes a quantum cascade laser, a micro electro mechanical system (MEMS) diffraction grating configured to include a diffraction/reflection portion that diffracts and reflects light emitted from the quantum cascade laser and to return a part of the light to the quantum cascade laser by swinging the diffraction/reflection portion, and a controller configured to control driving of the quantum cascade laser, wherein the controller is configured to pulse-drive the quantum cascade laser such that pulsed light of a second frequency higher than a first frequency at which the diffraction/reflection portion swings is emitted from the quantum cascade laser and a phase of the pulsed light changes each time the diffraction/reflection portion reciprocates m times (m: an integer of 1 or more).

In this external resonance type laser module, an external resonator is constituted by the MEMS diffraction grating, and thus the entire module may be miniaturized when compared to a case in which a diffraction grating, a rotation stage, an actuator, etc. are provided as the external resonator. In addition, because the quantum cascade laser is pulse-driven, a heating amount of the quantum cascade laser may be reduced when compared to a case in which the quantum cascade laser is continuously (CW) driven. As a result, it is possible to avoid an increase in size of a configuration for cooling the quantum cascade laser and to further miniaturize the entire module. In addition, it is possible to suppress occurrence of a defect in the quantum cascade laser due to an influence of heat, and to enhance reliability. Further, in this external resonance type laser module, the quantum cascade laser is pulse-driven such that pulsed light of a second frequency higher than a first frequency at which the diffraction/reflection portion swings is emitted from the quantum cascade laser and a phase of the pulsed light changes each time the diffraction/reflection portion reciprocates m times. In this way, it is possible to suppress occurrence of an omission in a wavelength spectrum of output light of the external resonance type laser module. As a result, it is possible to realize highly accurate measurement when the external resonance type laser module is used for spectroscopic analysis. As described above, according to this external resonance type laser module, it is possible to realize highly accurate measurement when the external resonance type laser module is used for the spectroscopic analysis while attempting miniaturization and improvement in reliability.

The controller may be configured to pulse-drive the quantum cascade laser such that the phase of the pulsed light changes by a predetermined value each time the diffraction/reflection portion reciprocates m times. In this way, it is possible to suppress occurrence of an omission in the wavelength spectrum of the output light by simple control.

The predetermined value may be equal to a pulse width of the pulsed light. In this way, it is possible to efficiently change the phase of the pulsed light.

The controller may be configured to pulse-drive the quantum cascade laser such that a point in time at which the pulsed light rises coincides with a point in time at which the diffraction/reflection portion turns back in an initial phase. In this way, it is possible to suppress occurrence of an omission in the wavelength spectrum of the output light by further simple control.

The MEMS diffraction grating may further include a movable portion with which the diffraction/reflection portion is provided, a support to which the movable portion is swingably coupled, and an actuator portion configured to swing the movable portion. In this way, it is possible to suitably miniaturize the entire module.

An analysis apparatus according to an aspect of the disclosure includes the external resonance type laser module described above, a photodetector configured to detect light output from the external resonance type laser module and transmitted through an analysis target, and a calculation unit configured to calculate an absorption spectrum based on a detection result of the photodetector, wherein the calculation unit is configured to calculate the absorption spectrum based on third data obtained by reversing first data obtained by the photodetector in one of a forward path period and a backward path period in swing of the diffraction/reflection portion with respect to time based on a point in time at which the forward path period and the backward path period are switched, and superimposing the first data on second data obtained by the photodetector in the other one of the forward path period and the backward path period.

In this analysis apparatus, the external resonance type laser module is included, and thus it is possible to realize highly accurate measurement while attempting miniaturization and improvement in reliability of the external resonance type laser module for the above-mentioned reason. In addition, in this analysis apparatus, the absorption spectrum is calculated based on the third data in which the first data and the second data obtained in the forward path period and the backward path period in swing of the diffraction/reflection portion are superimposed on each other. In this way, it is possible to improve measurement accuracy when compared to a case in which the absorption spectrum is calculated based on only one of the first data and the second data.

A method of driving an external resonance type laser module according to an aspect of the disclosure is a method of driving an external resonance type laser module, the external resonance type laser module including a quantum cascade laser and a MEMS diffraction grating configured to include a diffraction/reflection portion that diffracts and reflects light emitted from the quantum cascade laser and to return a part of the light to the quantum cascade laser by swinging the diffraction/reflection portion, and the method comprising pulse-driving the quantum cascade laser such that pulsed light of a second frequency higher than a first frequency at which the diffraction/reflection portion swings is emitted from the quantum cascade laser and a phase of the pulsed light changes each time the diffraction/reflection portion reciprocates m times (m: an integer of 1 or more).

In this method of driving the external resonance type laser module, the external resonance type laser module including the MEMS diffraction grating is driven. In this way, for the above-mentioned reason, it is possible to attempt miniaturization and improvement in reliability of the external resonance type laser module. In addition, in this method of driving the external resonance type laser module, the quantum cascade laser is pulse-driven such that pulsed light of a second frequency higher than a first frequency at which the diffraction/reflection portion swings is emitted from the quantum cascade laser and a phase of the pulsed light changes each time the diffraction/reflection portion reciprocates m times. In this way, it is possible to suppress occurrence of an omission in a wavelength spectrum of output light of the external resonance type laser module. As a result, it is possible to realize highly accurate measurement when the external resonance type laser module is used for spectroscopic analysis.

A program according to an aspect of the disclosure is a program for controlling driving of a quantum cascade laser in an external resonance type laser module including the quantum cascade laser and a MEMS diffraction grating configured to include a diffraction/reflection portion that diffracts and reflects light emitted from the quantum cascade laser and to return a part of the light to the quantum cascade laser by swinging the diffraction/reflection portion, wherein the program is configured to cause a computer to function as a controller that pulse-drives the quantum cascade laser such that pulsed light of a second frequency higher than a first frequency at which the diffraction/reflection portion swings is emitted from the quantum cascade laser and a phase of the pulsed light changes each time the diffraction/reflection portion reciprocates m times (m: an integer of 1 or more). In addition, an aspect of the disclosure is a computer-readable recording medium for recording the program.

DETAILED DESCRIPTION

Hereinafter, an embodiment of the disclosure will be described in detail with reference to drawings. In description below, the same reference numeral will be used for the same or a corresponding element, and a repeated description will be omitted.

[Configuration of Analysis Apparatus]

Figure 1:
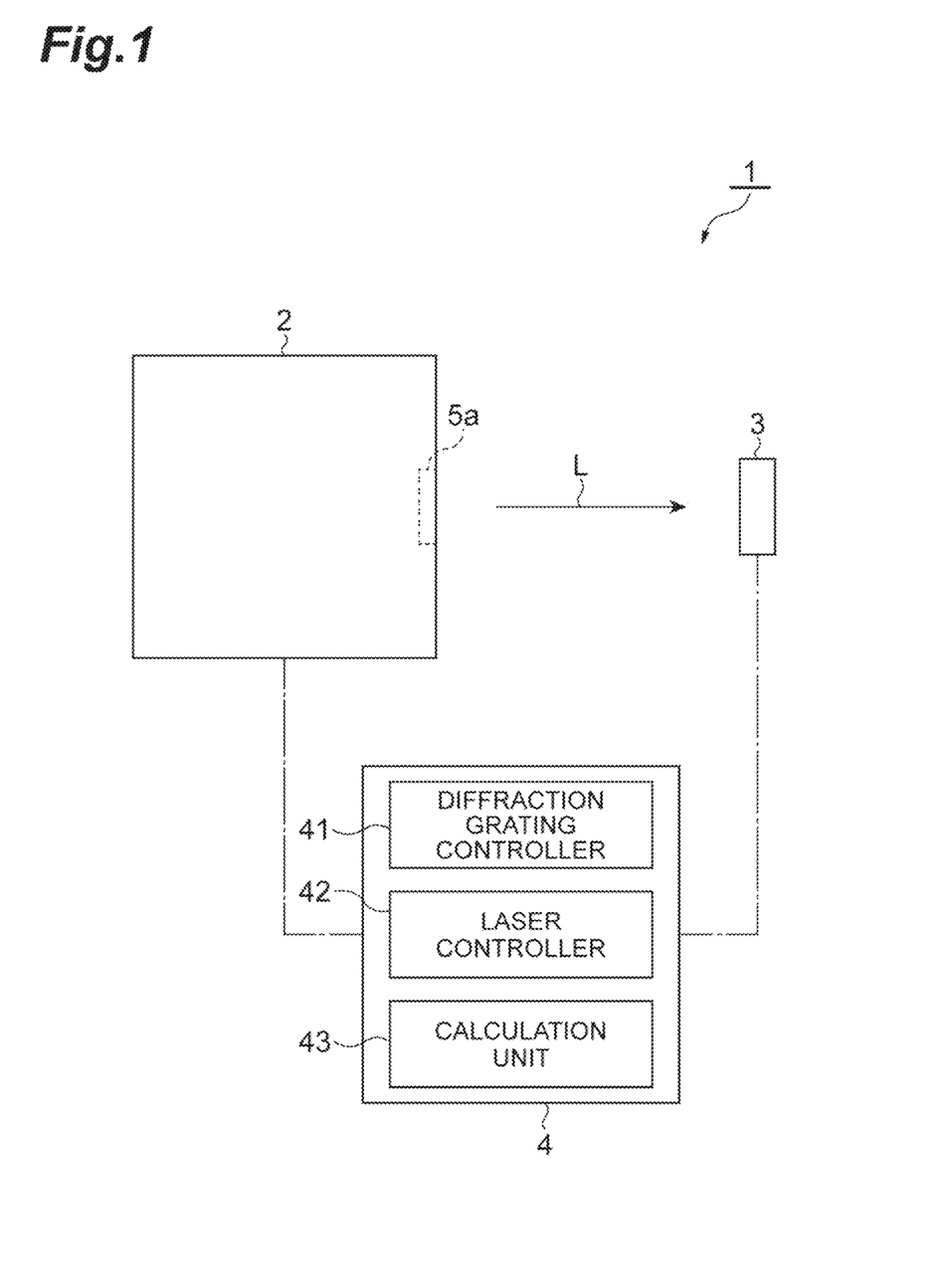
FIG. 1 is a configuration diagram of an analysis apparatus according to an embodiment of the disclosure.

As illustrated in FIG. 1, an analysis apparatus 1 includes an external resonance type laser module 2 (hereinafter referred to as a laser module 2), a photodetector 3, and a control device 4. The analysis apparatus 1 is an apparatus for performing spectroscopic analysis by measuring an absorption spectrum. For example, the analysis apparatus 1 is used in a state in which an analysis target accommodated in a light-transmitting container is disposed between the external resonance type laser module 2 and the photodetector 3. The analysis target may be any one of gas, liquid and solid.

The laser module 2 is a wavelength variable light source whose wavelength of output light L is variable. At the time of measuring the absorption spectrum, the laser module 2 performs wavelength sweeping in a predetermined wavelength range by changing the wavelength of the output light L at high speed. The photodetector 3 detects intensity of the output light L output from the laser module 2 and transmitted through the analysis target. For example, a mercury cadmium telluride (MCT) detector, an indium arsenide antimony (InAsSb) photodiode, a thermopile, etc. may be used as the photodetector 3. The control device 4 calculates the absorption spectrum based on a detection result of the photodetector 3. The control device 4 is electrically connected to the laser module 2 and the photodetector 3. Details of the control device 4 will be described below.

[Configuration of External Resonance Type Laser Module]

Figure 2:
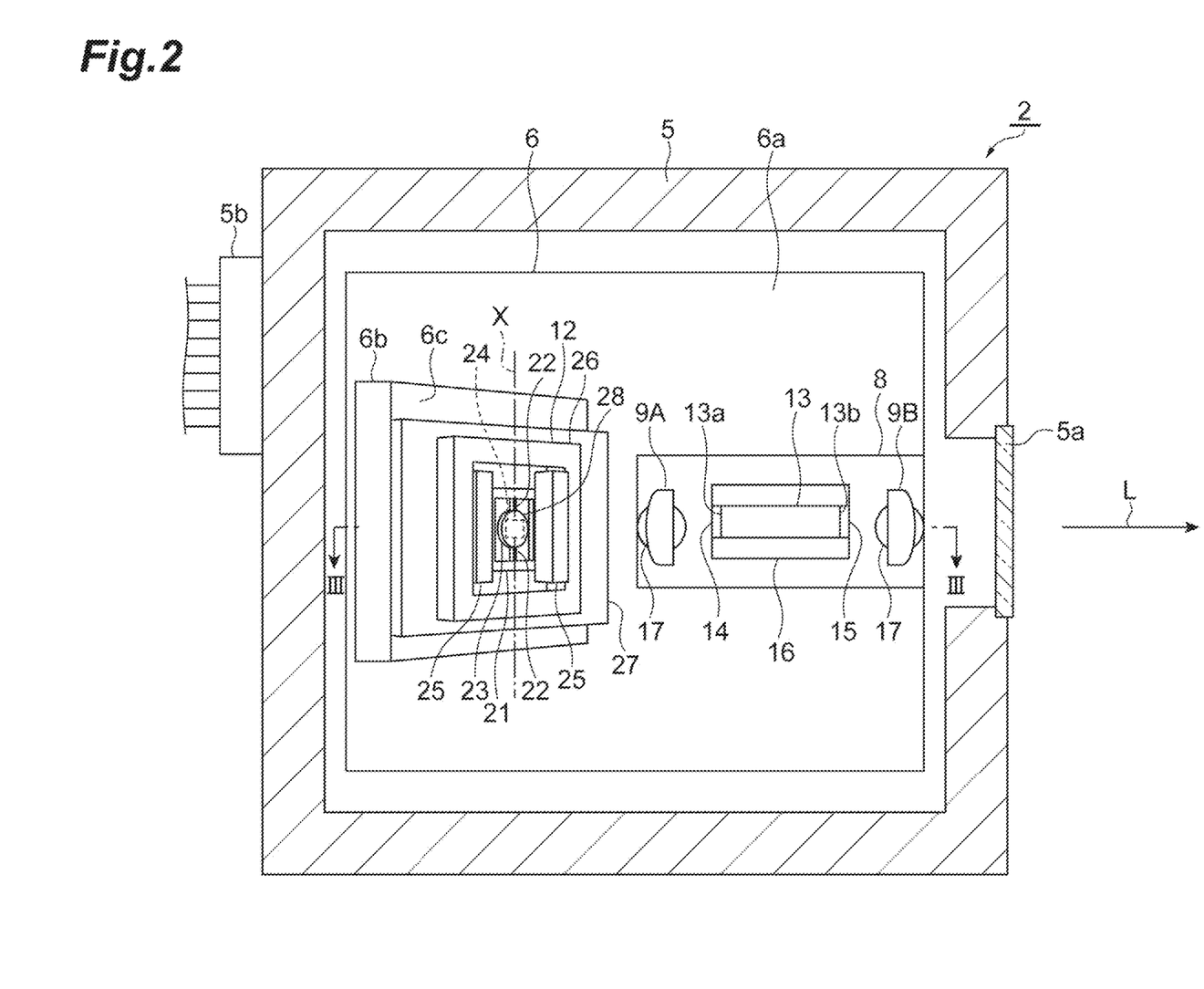
FIG. 2 is a cross-sectional view of an external resonance type laser module.
Figure 3:
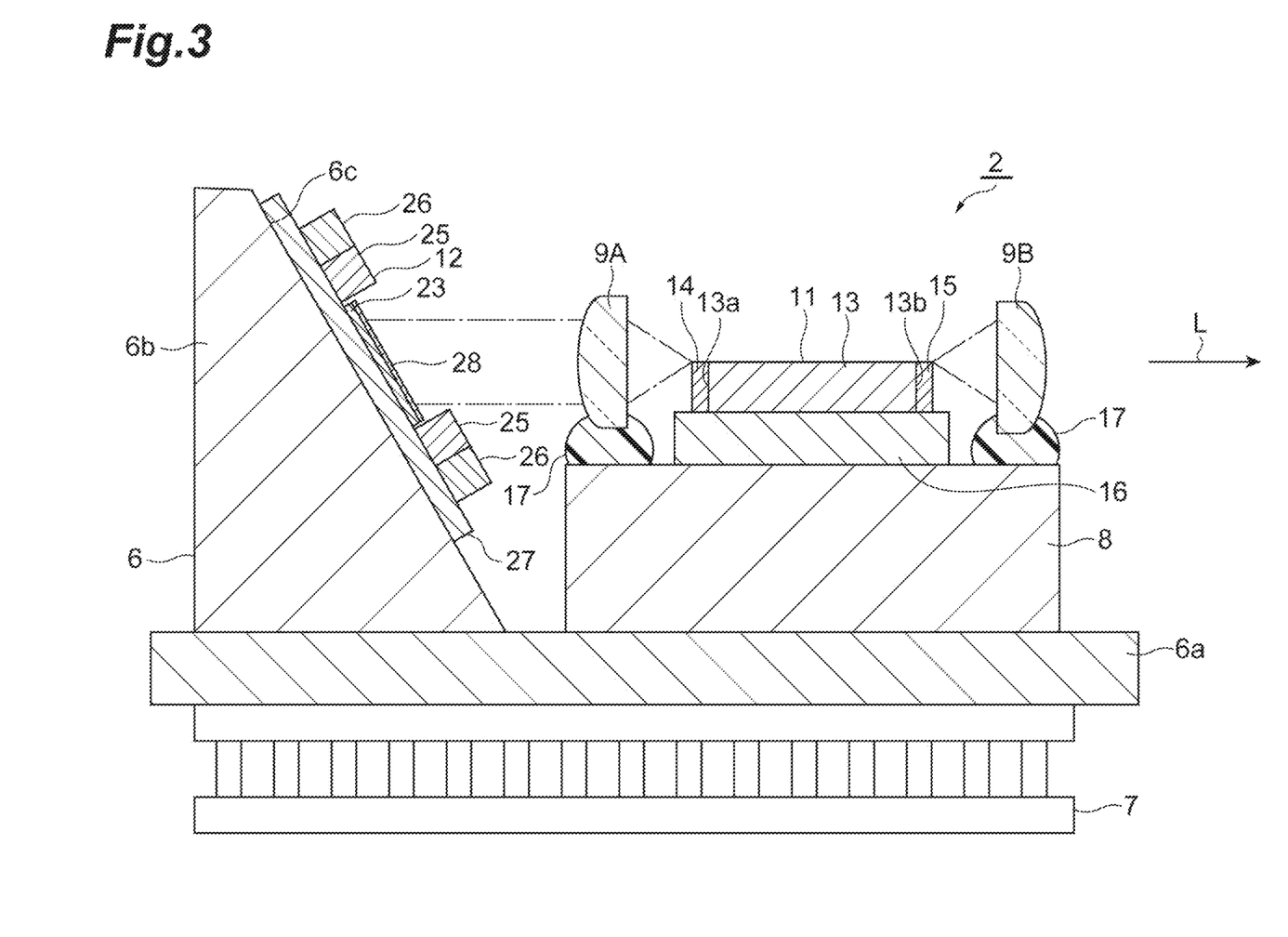
FIG. 3 is a cross-sectional view taken along III-III line of FIG. 2.

As illustrated in FIG. 2 and FIG. 3, the laser module 2 includes a housing 5, a base member 6, a cooler 7, a heat sink 8, lenses 9A and 9B, a quantum cascade laser 11 (hereinafter referred to as a "QCL 11"), and a MEMS diffraction grating 12. The housing 5 accommodates the base member 6, the cooler 7, the heat sink 8, the lenses 9A and 9B, the QCL 11 and the MEMS diffraction grating 12 therein. For example, the housing 5 is formed in a box shape and has a window 5a for outputting the output light L of the laser module 2 to the outside. In addition, a lead-out portion 5b for drawing out a wiring, etc. to the outside is provided with the housing 5. As an example, a length of each side of the housing 5 is about 70 mm.

For example, the base member 6 is made of aluminum (Al) and has a flat plate-shaped bottom wall portion 6a and a side wall portion 6b erected on the bottom wall portion 6a. The base member 6 is fixed on a bottom surface of the housing 5 with the cooler 7 interposed therebetween and is in contact with the cooler 7 in the bottom wall portion 6a. For example, the cooler 7 is a cooling device including a Peltier element. The side wall portion 6b has an inclined surface 6c inclined with respect to the bottom wall portion 6a. The MEMS diffraction grating 12 is fixed on the inclined surface 6c. A configuration of the MEMS diffraction grating 12 will be described below.

The QCL 11 has a quantum cascade laser element 13 (hereinafter referred to as a "QCL element 13"). The QCL element 13 has a first end surface 13a and a second end surface 13b facing each other and emits light in a wide band (for example, 3 μm or more and 20 μm or less) in a mid-infrared region from each of the first end surface 13a and the second end surface 13b. The QCL element 13 has a structure in which a plurality of active layers having different center wavelengths are stacked in a stacked manner, and can emit broadband light as described above. The QCL element 13 may have a structure including a single active layer. In this case as well, the QCL element 13 can emit wide-band light as described above.

A reflection reducing portion 14 is provided on the first end surface 13a of the QCL element 13. For example, the reflection reducing portion 14 includes an Anti Reflection (AR) layer whose reflectance is smaller than 0.5%. The reflection reducing portion 14 reduces the reflectance when light is emitted to the outside from the first end surface 13a of the QCL element 13 and reduces the reflectance when light is incident on the first end surface 13a of the QCL element 13 from the outside.

A reflection reducing portion 15 is provided on the second end surface 13b of the QCL element 13. For example, the reflection reducing portion 15 includes an AR layer whose reflectance is 2.5%. The reflection reducing portion 15 reduces the reflectance when light is emitted to the outside from the second end surface 13b of the QCL element 13. The reflection reducing portion 15 reflects a part of light emitted from the second end surface 13b of the QCL element 13 and transmits a remaining part. The light transmitted through the reflection reducing portion 15 becomes the output light L of the QCL 11. The reflection reducing portion 15 may not be provided on the second end surface 13b, and the second end surface 13b may be exposed.

The QCL 11 is fixed on the base member 6 with a sub-mount 16 and the heat sink 8 interposed therebetween. More specifically, the heat sink 8 is fixed on the bottom wall portion 6a of the base member 6, and the sub-mount 16 is fixed on the heat sink 8. The QCL 11 is fixed on the sub-mount 16. For example, the sub-mount 16 is a ceramic substrate including aluminum nitride (AlN). For example, the heat sink 8 is a heat dissipation member made of copper (Cu).

For example, the lenses 9A and 9B are aspherical lenses made of zinc selenide (ZnSe) or germanium (Ge) and are fixed on the heat sink 8 by an ultraviolet curable resin 17. The lens 9A is disposed on the first end surface 13a side with respect to the QCL element 13, and collimates light emitted from the first end surface 13a. The lens 9B is disposed on the second end surface 13b side with respect to the QCL element 13, and collimates light emitted from the second end surface 13b. The light collimated by the lens 9B is output to the outside through the window 5a of the housing 5.

The light collimated by the lens 9A is incident on the MEMS diffraction grating 12. The MEMS diffraction grating 12 diffracts and reflects this incident light, thereby returning light of a specific wavelength in the incident light to the first end surface 13a of the QCL element 13. That is, the MEMS diffraction grating 12 and the reflection reducing portion 15 constitute a Littrow-type external resonator. In this way, the laser module 2 can amplify light of a specific wavelength and output the light to the outside.

In addition, in the MEMS diffraction grating 12, as will be described below, it is possible to change a direction of a diffraction/reflection portion 28 that diffracts and reflects incident light at high speed. In this way, a wavelength of light returning from the MEMS diffraction grating 12 to the first end surface 13a of the QCL element 13 is variable, and consequently the wavelength of the output light L of the laser module 2 is variable.

The MEMS diffraction grating 12 includes a support 21, a pair of coupling portions 22 and 22, a movable portion 23, a coil 24 (actuator portion), a pair of magnets 25 and 25 (actuator portion), and a yoke 26. The MEMS diffraction grating 12 is configured as a MEMS device that swings the movable portion 23 around an axis X. The MEMS diffraction grating 12 is fixed on the inclined surface 6c of the base member 6 with a mounting member 27 interposed therebetween.

The mounting member 27 is a flat plate-shaped member having a substantially rectangular shape in a planar view (when viewed from a direction perpendicular to a plane on which at least the support 21 and the movable portion 23 are disposed).

The support 21 is a flat plate-shaped frame member having a rectangular shape in a planar view. The support 21 supports the movable portion 23, etc. via the pair of coupling portions 22. Each of the coupling portions 22 is a flat plate-shaped member having a rectangular shape in a planar view and extends along the axis X. Each of the coupling portions 22 connects the movable portion 23 to the support 21 on the axis X so that the movable portion 23 is swingable about the axis X.

The movable portion 23 is a flat plate-shaped member having a circular shape in a planar view, and is located inside the support 21. As described above, the movable portion 23 is swingably coupled to the support 21. For example, the support 21, the coupling portion 22, and the movable portion 23 are integrally formed by fabricating into one SOI substrate.

The diffraction/reflection portion 28 is provided on a surface of the movable portion 23 on the QCL 11 side. The diffraction/reflection portion 28 has a diffraction/reflection surface for diffracting and reflecting light emitted from the QCL 11. For example, the diffraction/reflection portion 28 is provided over the surface of the movable portion 23 and includes a resin layer on which a diffraction grating pattern is formed and a metal layer provided over a surface of the resin layer to extend along the diffraction grating pattern. Alternatively, the diffraction/reflection portion 28 may be provided on the movable portion 23 and includes only a metal layer on which a diffraction grating pattern is formed. Examples of the diffraction grating pattern include a blazed grating having a sawtooth cross section, a binary grating having a rectangular cross section, a holographic grating having a sinusoidal cross section, etc.

For example, the coil 24 is made of a metal material such as copper, and is embedded in a groove formed on the surface of the movable portion 23. The coil 24 is wound a plurality of turns in a spiral shape in a planar view. A wiring for connection with the outside is electrically connected to an outer end portion and an inner end portion of the coil 24. For example, the wiring is provided over the support 21, the coupling portion 22, and the movable portion 23, and is electrically connected to an electrode provided on the support 21.

The magnets 25 and 25 generate a magnetic field acting on the coil 24. The magnets 25 and 25 are formed in a rectangular parallelepiped shape and disposed to face a pair of side portions of the support 21, the side portions being parallel to the axis X in the support 21. For example, arrangement of magnetic poles of each magnet 25 corresponds to Halbach array. The yoke 26 amplifies a magnetic force of the magnet 25. The yoke 26 has a rectangular frame shape in a planar view and is disposed to surround the support 21 and the magnets 25 and 25.

In the MEMS diffraction grating 12, when a current flows through the coil 24, a Lorentz force is generated in a predetermined direction in electrons flowing in the coil 24 due to a magnetic field generated by the magnets 25 and 25. In this way, the coil 24 receives a force in the predetermined direction. For this reason, it is possible to swing the movable portion 23 (the diffraction/reflection portion 28) around the axis X by controlling the direction, magnitude, etc. of the current flowing through the coil 24. In addition, the movable portion 23 can be swung at a high speed at a resonance frequency level by applying a current having a frequency corresponding to a resonance frequency of the movable portion 23 to the coil 24. In this way, the coil 24 and the magnet 25 function as an actuator portion that causes the movable portion 23 to swing.

[Control of Analysis Apparatus]

The analysis apparatus 1 is controlled by the control device 4. As illustrated in FIG. 1, the control device 4 includes a diffraction grating controller 41 that controls driving of the MEMS diffraction grating 12, a laser controller 42 that controls driving of the QCL 11, and a calculation unit 43 that calculates an absorption spectrum based on a detection result of the photodetector 3. For example, the control device 4 may be constituted by a computer including an operation circuit such as a CPU on which operational processing is performed, a recording medium constituted by a memory such as a RAM and a ROM, and an input/output device. The control device 4 may be constituted by a computer such as a smart device including a smartphone, a tablet terminal, etc. The control device 4 can operate by causing the computer to read a program, etc. More specifically, the control device 4 may include a driver for driving the QCL 11, a function generator for generating a control pulse, a driver for controlling the cooler 7, etc. The function generator drives the QCL 11 and the MEMS diffraction grating 12 inter-connectedly by a program using output of two channels. The control device 4 may sample the output from the photodetector 3 by an oscilloscope or through an AD converter using a driving period of the MEMS diffraction grating 12 as a trigger. The diffraction grating controller 41, the laser controller 42, and the calculation unit 43 may not be constituted by a single computer, and may be constituted by separate computers or electronic circuits. For example, the diffraction grating controller 41 may be constituted by an electronic circuit included in the MEMS diffraction grating 12. In addition, the laser controller 42 may be constituted by an electronic circuit provided on the sub-mount 16 or a circuit board different from the sub-mount 16.

Figure 4:
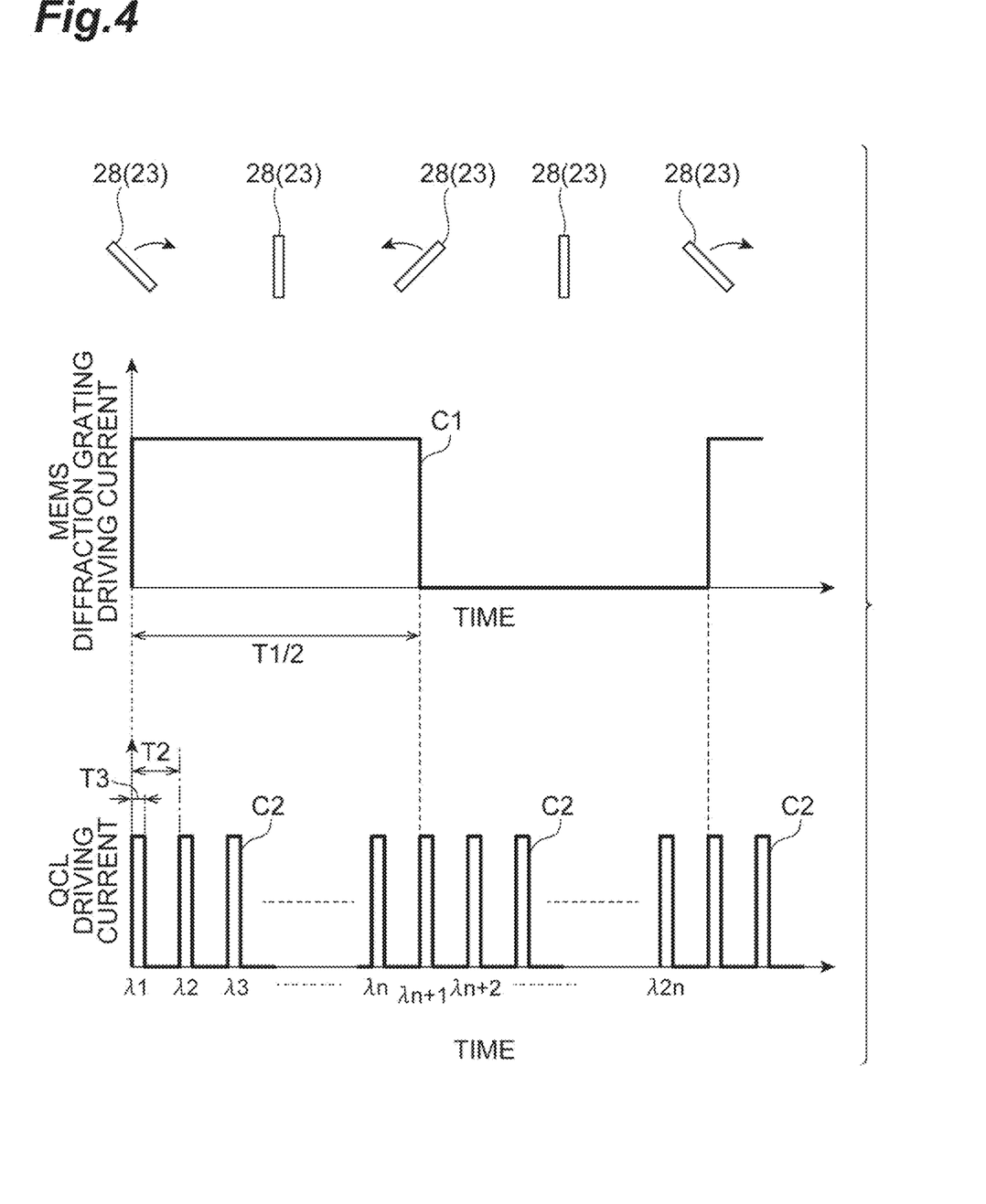
FIG. 4 is a diagram illustrating a method of driving a MEMS diffraction grating and a quantum cascade laser.

FIG. 4 is a diagram illustrating a method of driving the MEMS diffraction grating 12 and the QCL 11. As illustrated in FIG. 4, the diffraction grating controller 41 applies a pulsed driving current C1 of a first frequency f1 to the MEMS diffraction grating 12 (coil 24). In this way, as illustrated in an upper part of FIG. 4, the diffraction/reflection portion 28 (the movable portion 23) repeatedly and continuously swings at the first frequency f1. For example, the first frequency f1 is 0.5 kHz or more and 5 kHz or less. That is, a swinging period T1 ($=1/f1$) of the diffraction/reflection portion 28 is 0.2 ms or more and 2 ms or less.

The period T1 is a time required for the diffraction/reflection portion 28 to reciprocate once. The wavelength of the output light L of the laser module 2 changes in accordance with a rotation angle of the diffraction/reflection portion 28. The driving current C1 applied to the MEMS diffraction grating 12 is not limited to a pulse wave, and may be a sinusoidal wave, a triangular wave, or a sawtooth wave.

The laser controller 42 applies a pulsed driving current C2 having a second frequency f2 higher than the first frequency f1 to the QCL 11 (QCL element 13). In this way, pulsed light of the second frequency f2 is emitted from the QCL 11. That is, a waveform of the pulsed light emitted from the QCL 11 is similar to a waveform of the driving current C2. For example, the second frequency f2 is 5 kHz or more and 10 MHz or less. That is, a period T2 ($=1/f2$) of the pulsed light is 0.1 μs or more and 0.2 ms or less. For example, a pulse width T3 of the pulsed light is 500 ns or less. For example, a duty cycle (duty ratio) ($=T3/T2$) which is a ratio of the pulse width T3 in the period T2 is larger than 0% and 10% or less. FIG. 4 illustrates the driving current C2 at an initial phase before a phase of the pulsed light is changed as described below. In this example, at the initial phase, a point in time at which the pulsed light rises coincides with a point in time at which the diffraction/reflection portion 28 turns back.

When the QCL 11 is driven as described above, pulsed light is emitted from the QCL 11 n times (n=(T1/2)/T2) in a forward path period (that is, during T1/2) in swing of the diffraction/reflection portion 28. In this instance, because the rotation angle of the diffraction/reflection portion 28 differs depending on the emission timing of each light, wavelengths of the output light L corresponding to lights successively emitted from the QCL 11 become different values of $\lambda 1, \lambda 2, \lambda 3, \ldots, \lambda n$. For example, when the output light L is swept from a short wavelength side in order, the wavelengths $\lambda 1, \lambda 2, \lambda 3, \ldots, \lambda n$ satisfy a relationship of $\lambda 1 < \lambda 2 < \lambda 3 < \ldots < \lambda n$.

Meanwhile, pulsed light is emitted from the QCL 11 n times in a backward path period in swing of the diffraction/reflection portion 28. When the output light L is swept from a short wavelength side in order in the forward path period as described above, wavelengths $\lambda n+1, \lambda n+2, \ldots, \lambda 2n$ of the output light L corresponding to lights successively emitted from the QCL 11 satisfy a relationship of $\lambda n+1 > \lambda n+2 > \ldots > \lambda 2n$ in the backward path period contrary to the forward path period.

Here, the wavelengths $\lambda n+1, \lambda n+2, \ldots, \lambda 2n$ of the output light L in the backward path period are approximately equal to wavelengths obtained by reversing the wavelengths $\lambda 1, \lambda 2, \lambda 3, \ldots, \lambda n$ of the output light L in the forward path period with respect to time based on a point in time at which the forward path period and the backward path period are switched. For this reason, in the analysis apparatus 1 of the present embodiment, the calculation unit 43 calculates the absorption spectrum using only data obtained by the photodetector 3 in one of the forward path period and the backward path period (for example, the forward path period). In this way, it possible to reduce the number of samples, and to simplify the calculation of the absorption spectrum.

Figure 5:
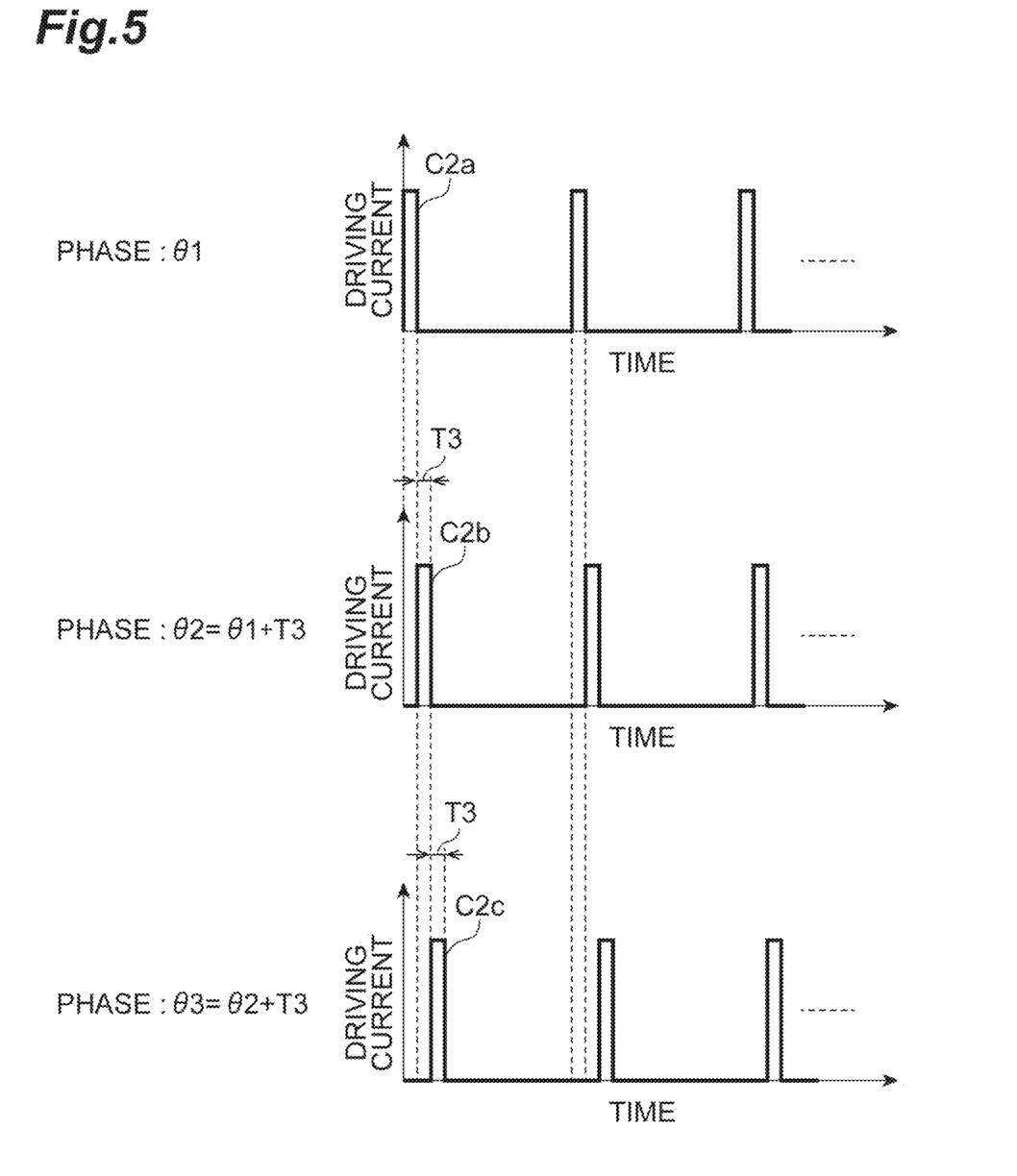
FIG. 5 is a diagram illustrating a method of driving the quantum cascade laser.

Further, as illustrated in FIG. 5, the laser controller 42 pulse-drives the QCL 11 so that the phase of the pulse light emitted from the QCL 11 changes (shifts) by the pulse width T3 each time the diffraction/reflection portion 28 reciprocates once. More specifically, the laser controller 42 changes the phase of the driving current C2 applied to the QCL 11 by the pulse width T3 each time the diffraction/reflection portion 28 reciprocates once. In this way, the driving current C2 shift by the pulse width T3 each time the diffraction/reflection portion 28 reciprocates once, such as from a driving current C2a (phase: θ1), to a driving current C2b (phase: θ2=θ1+T3), to a driving current C2c (phase: θ3=θ2+T3). In this instance, in accordance with the change in the phase of the driving current C2, the phase of the pulsed light emitted from the QCL 11 changes by the pulse width T3. When the change in the phase is repeated p−1 times (p=T2/T3), the wavelength spectrum of the output light L is filled without any gap on a time axis, and continuous wavelength sweeping is apparently realized. For this reason, the calculation unit 43 may calculate the absorption spectrum based on the detection result of the photodetector 3 while the phase of the pulsed light changes at least p−1 times from an initial phase. A process of changing the phase of the pulsed light is not limited to p−1 times, and may be repeatedly executed until the process is completed.

Figure 6:
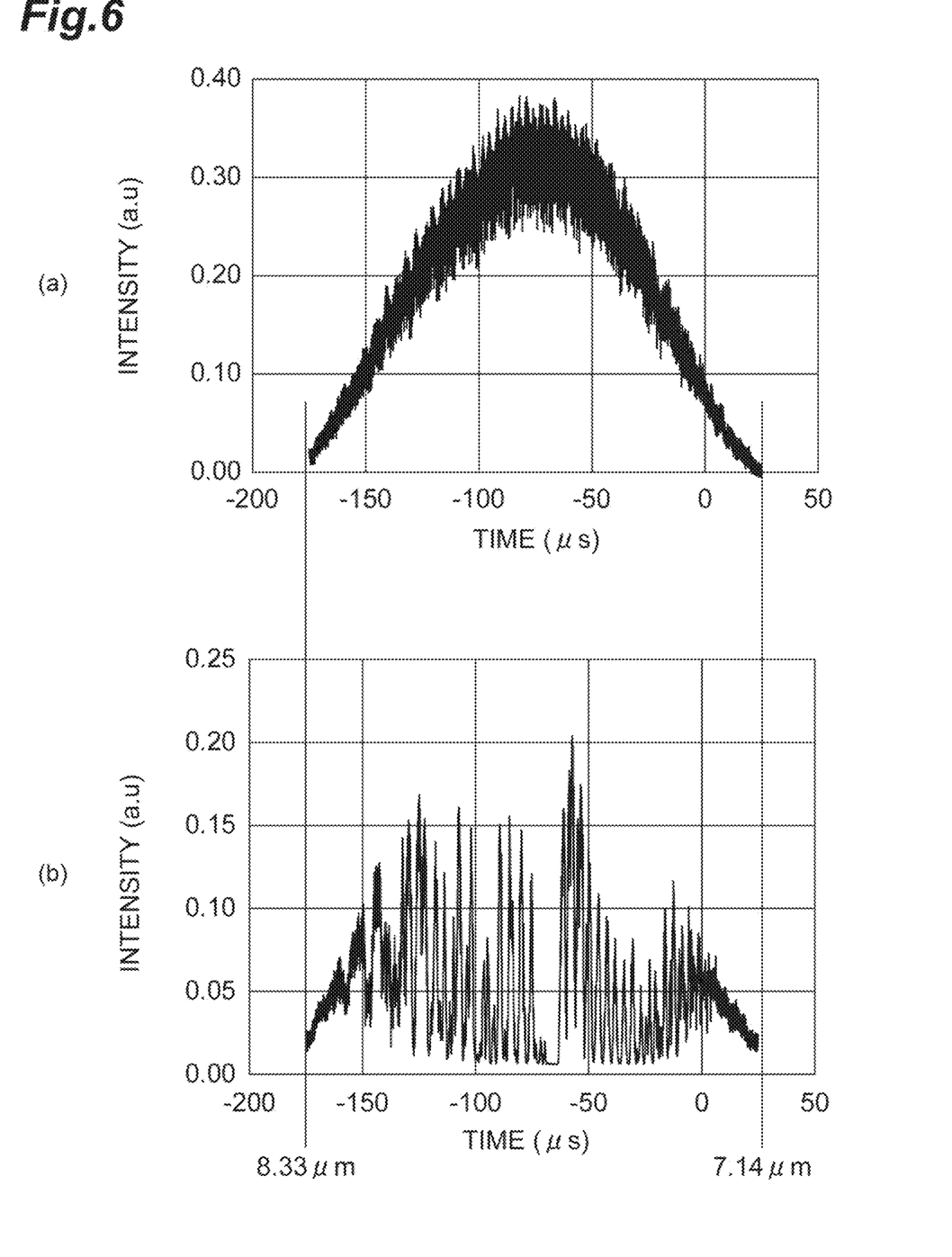
FIG. 6 are graphs illustrating a result of measuring an absorption spectrum of atmosphere and methane using the analysis apparatus of FIG. 1.
Figure 7A:
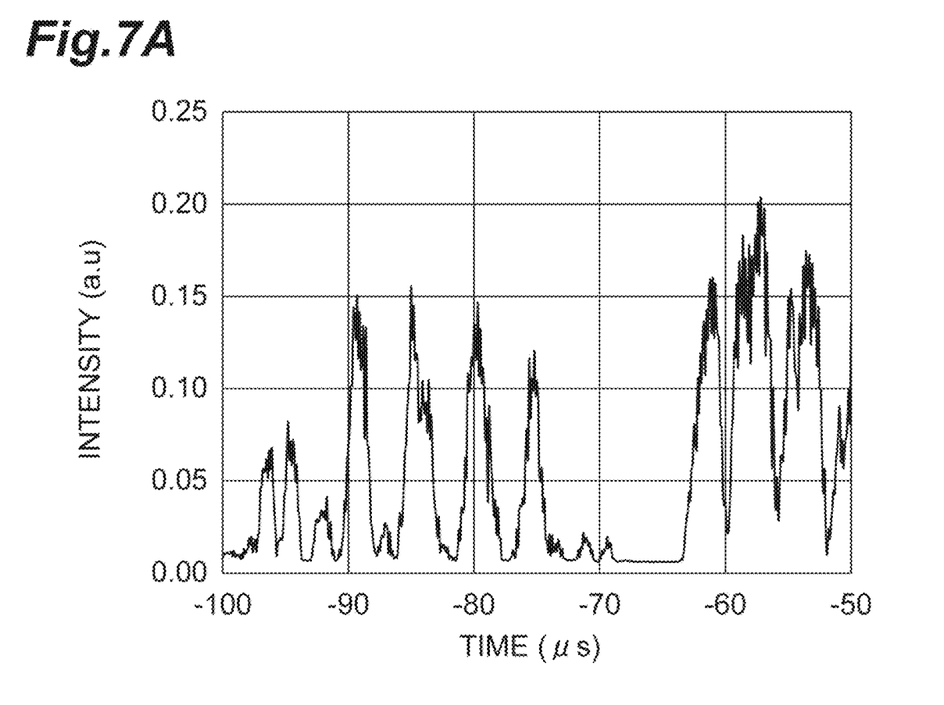
FIG. 7A is a graph illustrating a result of measuring an absorption spectrum of methane using the analysis apparatus of FIG. 1.
Figure 7B:
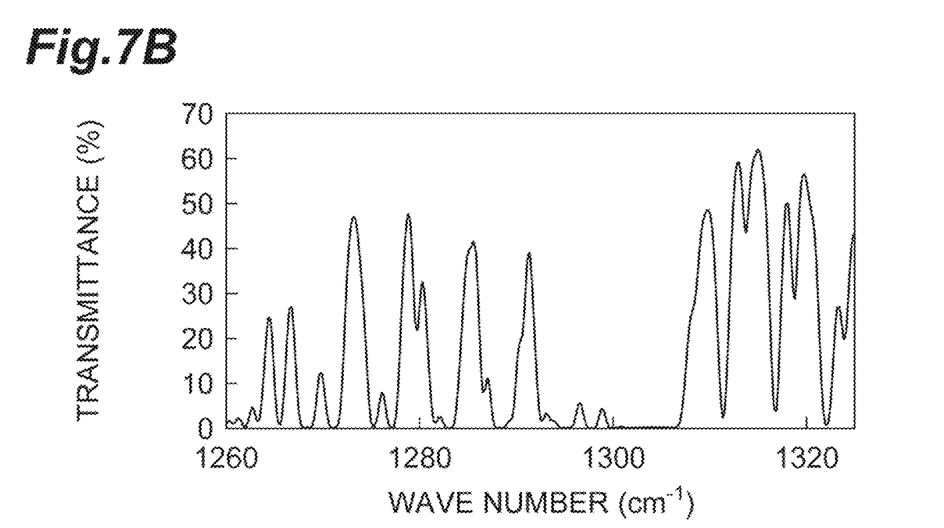
FIG. 7B is a graph illustrating a result of measuring an absorption spectrum of methane using a Fourier transform infrared spectroscopy (FTIR).

Graph (a) of FIG. 6 illustrates results of measuring absorption spectra of atmosphere using the analysis apparatus 1 and graph (b) of FIG. 6 illustrates results of measuring absorption spectra of methane using the analysis apparatus 1. FIG. 7A is a graph illustrating a result of measuring an absorption spectrum of methane using the analysis apparatus 1, and FIG. 7B is a graph illustrating a result of measuring an absorption spectrum of methane using an FTIR. In FIG. 6, positions at which wavelengths of the output light L correspond to 7.14 μm and 8.33 μm are indicated.

In examples illustrated in FIG. 6 and FIG. 7A, a QCL having a wavelength of 7 μm band is used as the QCL 11, the first frequency f1 is set to 1 kHz (the period T1 is set to 1 ms), the second frequency f2 is set to 100 kHz (the period T2 is set to 10 μs), and the pulse width T3 is set to 100 ns. In this case, the duty cycle is 1%, and the number of times of change of the phase of the pulsed light necessary for filling the wavelength spectrum of the output light L without any gap is 99 times. In addition, for example, a maximum value of the rotation angle of the diffraction/reflection portion 28 is about 10 degrees. In this example, the QCL 11 is pulse-driven so that the phase of the pulsed light emitted from the QCL 11 changes by the pulse width T3 each time the diffraction/reflection portion 28 reciprocates 10 times. In this case, because the period T1 is 1 ms, it is possible to acquire an absorption spectrum accumulated ten times along the time axis by driving for one second.

It is understood from FIG. 6 that the absorption spectra of atmosphere and methane may be accurately measured using the analysis apparatus 1. In addition, it is understood from FIG. 7A and FIG. 7B that the absorption spectrum may be measured at the same degree of accuracy as that of a case in which the FTIR is used by the analysis apparatus 1.

Figure 8:
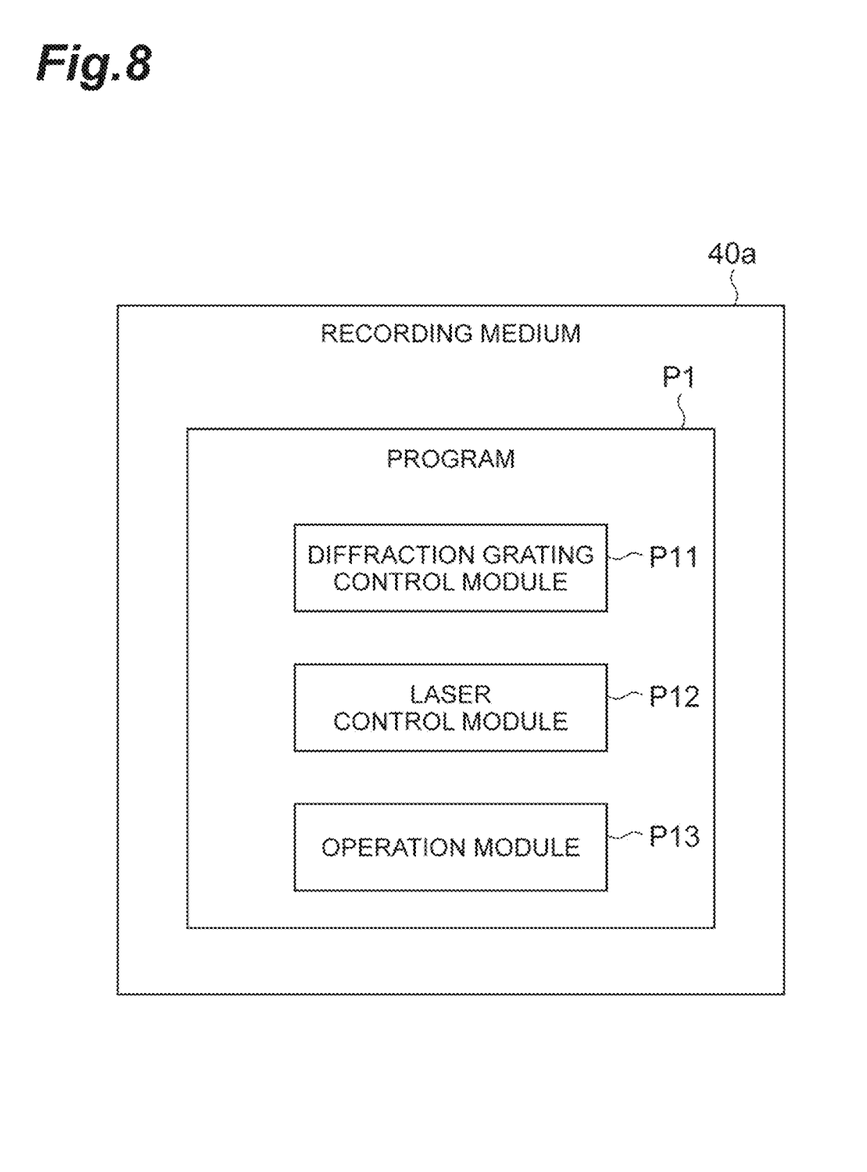
FIG. 8 is a diagram illustrating a recording medium in which a program is stored.

FIG. 8 is a diagram illustrating a recording medium 40a in which a program P1 for causing the computer to function as the control device 4 is stored. The program P1 stored in the recording medium 40a includes a diffraction grating control module P11, a laser control module P12, and an operation module P13. Functions realized by executing the diffraction grating control module P11, the laser control module P12, and the operation module P13 are similar to functions of the diffraction grating controller 41, the laser controller 42, and the calculation unit 43. For example, the program P1 may be provided by a recording medium such as a CD-ROM, a DVD, or a ROM, or a semiconductor memory. A method of controlling the analysis apparatus 1 (method of driving the laser module 2) executed in the control device 4 may be executed based on the program P1 stored in the recording medium 40a.

[Function and Effect]

In the laser module 2 described above, because the external resonator is constituted by the MEMS diffraction grating 12, the entire laser module 2 may be miniaturize when compared to a case in which a diffraction grating, a rotation stage, an actuator, etc. are provided as the external resonator. In addition, in the laser module 2, because the QCL 11 is pulse-driven, a heating amount of the QCL 11 may be reduced when compared to a case in which the QCL 11 is continuously driven. As a result, it is possible to avoid an increase in size of a configuration for cooling the QCL 11 and to further miniaturize the entire module. That is, in the laser module 2, it is possible to omit a secondary cooling device such as a cooling water chiller or an air cooling fan, and a power supply for driving the cooling water chiller or the air cooling fan. In addition, it is possible to suppress occurrence of a defect in the QCL 11 due to an influence of heat, and to enhance reliability. Examples of the defect due to the influence of heat may include deterioration of the reflection reducing portion 14 or the reflection reducing portion 15. In addition, when the QCL 11 is driven with a short pulse and a low duty cycle, a thermal load is small, and thus the cooler 7 can be omitted. In this case, it is possible to omit the cooler 7 and a driver for controlling the cooler 7, and to further miniaturize the entire module.

In addition, if the QCL 11 is continuously pulse-driven at a constant phase, the wavelength of the output light L of the laser module 2 is intermittently swept, and an omission (flaw) occurs in the wavelength spectrum of the output light L. In this case, there is concern that an omission may occur in an absorption spectrum calculated by the calculation unit 43, and measurement accuracy may decrease. In this regard, in the laser module 2 of the present embodiment, the pulsed light of the second frequency higher than the first frequency f1 at which the diffraction/reflection portion 28 swings is emitted from the QCL 11, and the QCL 11 is pulse-driven such that the phase of the pulsed light changes by the pulse width T3 each time the diffraction/reflection portion 28 reciprocates once. In this way, as described above, it is possible to suppress occurrence of an omission in the wavelength spectrum of the output light L of the laser module 2, and to realize highly accurate measurement. Therefore, according to the laser module 2, it is possible to realize highly accurate measurement when the external resonance type laser module is used for the spectroscopic analysis while attempting miniaturization and improvement in reliability.

In addition, in the laser module 2, the laser controller 42 pulse-drives the QCL 11 such that a point in time at which the pulsed light rises coincides with a point in time at which the diffraction/reflection portion 28 turns back in the initial phase. In this way, it is possible to suppress occurrence of an omission in the wavelength spectrum of the output light L by simple drive control.

In addition, in the laser module 2, the MEMS diffraction grating 12 includes the movable portion 23 in which the diffraction/reflection portion 28 is provided, the support 21 to which the movable portion 23 is swingably coupled, and the actuator portion (the coil 24 and the magnet 25) that swings the movable portion 23. In this way, the entire module may be suitably miniaturized.

In addition, according to the analysis apparatus 1 using the laser module 2, it is possible to attempt miniaturization, high speed, and high resolution when compared to the FTIR, and to realize real-time measurement in a field which may not be realized by the FTIR. That is, while time is required for movement of a moving mirror in measurement in the FTIR because interference waveforms are detected by moving the moving mirror, substantially real-time measurement may be performed in the analysis apparatus 1 because high-speed wavelength sweeping is performed by the MEMS diffraction grating 12. In addition, in the FTIR, measurement accuracy (wavelength resolution) depends on the moving distance of the moving mirror. Thus, a long moving distance needs to be ensured to perform measurement at high accuracy, and there is concern that an apparatus configuration may become large, and measurement time may become long. For this reason, when compared to an apparatus having the same size, far more accurate measurement than that in the FTIR may be performed in the analysis apparatus 1. A problem that an omission occurs in a wavelength spectrum of the output light L described above is a problem unique to a case in which the MEMS diffraction grating 12 that repeatedly and continuously swings the diffraction/reflection portion 28 is used as the external resonator, and does not occur when the diffraction grating is rotated by a device capable of directly controlling a rotation angle of a motor, a piezo element, etc.

[Modification]

An embodiment of the disclosure has been described above. However, the disclosure is not limited to the embodiment. For example, a method of controlling the QCL 11 is not limited to the above-described example. The QCL 11 may be driven so that the wavelength spectrum of the output light L is filled on the time axis, and the phase of the pulsed light may change by the pulse width T3 each time the diffraction/reflection portion 28 reciprocates m times (m: an integer of 1 or more). In addition, each time the diffraction/reflection portion 28 reciprocates m times, the phase of the pulsed light may change by a predetermined value other than the pulse width T3. For example, the predetermined value may be a value smaller than the pulse width T3, or may be a value larger than the pulse width T3. Alternatively, the predetermined value may be a negative value. Further, each time the diffraction/reflection portion 28 reciprocates m times, the phase of the pulsed light may randomly change. For example, the phase of the pulsed light may change by a randomly selected value. In these cases, when the phase of the pulsed light is repeatedly changed, it is possible to fill the wavelength spectrum of the output light L on the time axis without any gap or to some extent. In a case in which the phase of the pulsed light is changed by a predetermined value, it is possible to suppress occurrence of an omission in the wavelength spectrum of the output light L by simple control when compared to a case in which the phase is randomly changed. In addition, when the phase of the pulsed light is changed by the pulse width T3 as in the above embodiment, it is possible to efficiently change the phase of the pulsed light.

In the above embodiment, a point in time at which the pulsed light rises coincides with a point in time at which the diffraction/reflection portion 28 turns back in the initial phase. However, these points in time may not coincide with each other. In addition, a timing of changing the phase of the pulsed light may not coincide with a point in time at which the forward path period and the backward path period are switched in swing of the diffraction/reflection portion 28, and the phase of the pulsed light may be changed at one point in the forward path period or the backward path period.

In the above embodiment, the calculation unit 43 calculates the absorption spectrum using only data obtained by the photodetector 3 in any one of the forward path period and the backward path period. However, the absorption spectrum may be calculated based on third data obtained by reversing first data obtained by the photodetector 3 in any one of the forward path period and the backward path period (for example, the backward path period) in swing of the diffraction/reflection portion 28 with respect to time based on a point in time at which the forward path period and the backward path period are switched, and superimposing the first data on second data obtained by the photodetector 3 in the other one of the forward path period and the backward path period (for example, the forward path period). In this case, when compared to a case in which an absorption spectrum is calculated based on only one of the first data and the second data, it is possible to acquire a twice more integrated spectrum, and to improve measurement accuracy.

In the above embodiment, the external resonator may be configured in a Littman type. A material and a shape of each configuration are not limited to the above-described material and shape, and it is possible to adopt various materials and shapes. For example, the movable portion 23 may have a rectangular shape in a planar view. In the above embodiment, the MEMS diffraction grating 12 is configured in an electromagnetic drive type; however, it may be configured in an electrostatic drive type. In this case, for example, the actuator portion of the MEMS diffraction grating 12 may be constituted by a comb-shaped electrode pair.

According to an aspect of the disclosure, it is possible to provide an external resonance type laser module capable of realizing highly accurate measurement when used for spectroscopic analysis while attempting miniaturization and improvement in reliability.

What is claimed is:

1. An external resonance type laser module comprising:
a quantum cascade laser;
a MEMS diffraction grating configured to include a diffraction/reflection portion that diffracts and reflects light emitted from the quantum cascade laser and to return a part of the light to the quantum cascade laser by swinging the diffraction/reflection portion; and
a controller configured to control driving of the quantum cascade laser,
wherein the controller is configured to pulse-drive the quantum cascade laser such that pulsed light of a second frequency higher than a first frequency at which the diffraction/reflection portion swings is emitted from the quantum cascade laser, and
wherein the controller is configured to pulse-drive the quantum cascade laser such that a phase of the pulsed light changes each time the diffraction/reflection portion reciprocates m times, where m is an integer of 1 or more.

2. The external resonance type laser module according to claim 1, wherein the controller is configured to pulse-drive the quantum cascade laser such that the phase of the pulsed light changes by a predetermined value each time the diffraction/reflection portion reciprocates m times.

3. The external resonance type laser module according to claim 2, wherein the predetermined value is equal to a pulse width of the pulsed light.

4. The external resonance type laser module according to claim 1, wherein the controller is configured to pulse-drive the quantum cascade laser such that a point in time at which the pulsed light rises coincides with a point in time at which the diffraction/reflection portion turns back in an initial phase.

5. The external resonance type laser module according to claim 1, wherein the MEMS diffraction grating further includes a movable portion with which the diffraction/reflection portion is provided, a support to which the movable portion is swingably coupled, and an actuator portion configured to swing the movable portion.

6. An analysis apparatus comprising:

the external resonance type laser module according to claim 1;

a photodetector configured to detect light output from the external resonance type laser module and transmitted through an analysis target; and a calculation unit configured to calculate an absorption spectrum based on a detection result of the photodetector, wherein the calculation unit is configured to calculate the absorption spectrum based on third data obtained by reversing first data obtained by the photodetector in one of a forward path period and a backward path period in swing of the diffraction/reflection portion with respect to time based on a point in time at which the forward path period and the backward path period are switched, and superimposing the first data on second data obtained by the photodetector in the other one of the forward path period and the backward path period.

7. A method of driving an external resonance type laser module, the external resonance type laser module including a quantum cascade laser and a MEMS diffraction grating configured to include a diffraction/reflection portion that diffracts and reflects light emitted from the quantum cascade laser and to return a part of the light to the quantum cascade laser by swinging the diffraction/reflection portion, the method comprising:

pulse-driving the quantum cascade laser such that pulsed light of a second frequency higher than a first frequency at which the diffraction/reflection portion swings is emitted from the quantum cascade laser; and pulse-driving the quantum cascade laser such that a phase of the pulsed light changes each time the diffraction/reflection portion reciprocates m times, where m is an integer of 1 or more.

8. A non-transitory computer readable medium that stores a program for controlling driving of a quantum cascade laser in an external resonance type laser module including the quantum cascade laser and a MEMS diffraction grating configured to include a diffraction/reflection portion that diffracts and reflects light emitted from the quantum cascade laser and to return a part of the light to the quantum cascade laser by swinging the diffraction/reflection portion, wherein the program is configured to cause a computer to function as a controller that pulse-drives the quantum cascade laser such that pulsed light of a second frequency higher than a first frequency at which the diffraction/reflection portion swings is emitted from the quantum cascade laser and a phase of the pulsed light changes each time the diffraction/reflection portion reciprocates m times, where m is an integer of 1 or more.

* * * * *